United States Patent [19]

Brunsch et al.

[11] Patent Number: 4,651,092
[45] Date of Patent: Mar. 17, 1987

[54] METHOD OF DETERMINING DISPERSION, PARTICLE DENSITY OR VISCOSITY OF RESIN/SOLVENT MIXTURE CONTAINING MAGNETIC PARTICLES

[75] Inventors: Arwed Brunsch, Stuttgart; Werner Steiner, Boeblingen; Gerhard Trippel, Sindelfingen, all of Fed. Rep. of Germany

[73] Assignee: International Business Machines Corporation, Armonk, N.Y.

[21] Appl. No.: 534,471

[22] Filed: Sep. 21, 1983

[30] Foreign Application Priority Data

Sep. 22, 1982 [EP] European Pat. Off. ........ 82108769.9

[51] Int. Cl.$^4$ .................. G01N 27/74; G01R 33/12
[52] U.S. Cl. ..................................... 324/204; 324/239
[58] Field of Search ............... 324/201, 228, 233, 239, 324/204, 214, 215, 216, 232; 118/689

[56] References Cited

U.S. PATENT DOCUMENTS

| | | | |
|---|---|---|---|
| 2,878,444 | 3/1959 | Feher | 324/201 |
| 3,534,256 | 10/1970 | Johnson, Jr. | 324/201 |
| 3,586,963 | 6/1971 | Arrott et al. | 324/243 |
| 4,523,146 | 6/1985 | Champaigne | 324/236 |

FOREIGN PATENT DOCUMENTS 565243 7/1977 U.S.S.R. ............................ 324/201

OTHER PUBLICATIONS

Tso, "Toner Concentration Meter", Xerox Disclosure Journal, vol. 5, No. 3, May/Jun. 1980, pp. 315-316.

Primary Examiner—Ernest F. Karlsen
Assistant Examiner—Walter E. Snow
Attorney, Agent, or Firm—Walter J. Madden, Jr.; Thomas R. Berthold

[57] ABSTRACT

For characterizing coating compositions with magnetic particles the coating composition is subjected to an alternating magnetic field of variable frequency. The field induced by the coating composition after energization is recorded, and thus the susceptibility of the coating composition is measured. Depending on the variable frequency, conclusions can be made regarding the degree of dispersion, particle density, and viscosity of the coating composition. The variable frequency is between 1 and 100 cps, and the field intensity of the energizing field should be lower than 10 Oerstedt. The coating composition is fluid or stagnant in a pipe *1, 11 which is surrounded by field coil and measuring coil.

5 Claims, 4 Drawing Figures

METHOD OF DETERMINING DISPERSION, PARTICLE DENSITY OR VISCOSITY OF RESIN/SOLVENT MIXTURE CONTAINING MAGNETIC PARTICLES

BACKGROUND OF THE INVENTION

1. Field Of The Invention

The invention refers to an arrangement for characterizing magnetic coating compositions consisting of a dispersion of magnetic particles, particularly $\gamma\text{-Fe}_2\text{O}_3$ pigment, in a liquid resin-solvent mixture.

Such coating compositions containing magnetic particles are widely used for making magnetic record carriers, in particular magnetic disks and magnetic tapes. After the application of the magnetic coating composition on the carrier, the majority of the solvent evaporates. During or after the application of the coating composition and the evaporation of the solvent, there takes place an orientation of the magnetic particles, the firing and polishing of the record carrier, if necessary a lubrication of the surface, and finally a test for the magnetic characteristics of the record carrier. The quality of the magnetic coating composition is of decisive importance for the quality of the magnetic record carrier.

The magnetic coating composition is generally made using methods of paint production. Apart from precisely observing the chemical composition, it is of great importance to implement a complicated mechanical processing. This, and the physical-chemical characteristics of the components of the coating composition, as well as their interaction, determine the internal structure of the coating composition, with the degree of dispersion and of agglomeration of the individual particles playing an important part.

For these characteristics which strongly influence the quality of the finished record carrier there do not yet exist any direct measuring means. The viscosity of the coating composition which very much depends on the internal structure influences the processing characteristics. Electrostatic and magnetostatic forces between the particles can cause aging which only becomes visible later in the finished record carrier.

The quality of the coating composition is at present tested in production in that a control record carrier is made which substantially corresponds to a finished record carrier, and that the latter is then tested for quality. Further use of the coating composition depends on this check. It is obvious that such a test is very time-consuming, expensive and imprecise since immediately before, and during the application of the coating composition on the carrier, no measure of the quality of the coating composition is available.

Decisive factors for the quality of the magnetic coating composition are the degree of dispersion or of agglomeration, respectively, the particle density, and the viscosity. Furthermore, the stability of the composition plays a part which strongly depends on time, i.e. what is the stability of the coating composition during a predetermined period, or in other words, does the coating composition age prematurely, and if so, to what extent?

German Pat. No. 17 98 223 teaches a method of continuously controlling the homogenizing of mixtures composed of two or more substances. For that purpose, a powdery magnetically oriented substance is added as indicator to the mixture to be homogenized. By means of a measuring unit in the device, the intensity of the magnetic field is traced. With this method, the macroscopic dispersion of the indicator in the mixture is observed in which the magnetic density is measured. However, this method does not give any information on the microscopic distribution and the state of the individual particles.

German Offenlegungsschrift No. 20 49 463 discloses a method for the dispersion analysis of suspensions. There, the degree of dispersion of the suspension is determined according to the maximum layer thickness of a suspension applied on a substrate by means of a doctor blade, the substrate being moved continuously in one direction under the doctor blade. The disadvantage of this method is that for control purposes suspension has to be continuously withdrawn, and that furthermore it is very complicated to make a desired very low wedge layer thickness of a few $\mu m$.

German pat. No. 23 37 165 describes a method and a device for measuring the electrokinetic zeta-potential of a dispersion. From the dispersion to be examined, a sample stream is continuously removed and sent through a separator cell, where it is exposed to a magnetic field and divided into several part streams. These part streams are subsequently directed through individual separate measuring cells where the solid composition content of the individual part streams is determined continuously. A measuring according to this method determines the electrostatic charge of the pigments with respect to the resin binder system, and it characterizes the stability of the dispersion but not its dispersion degree.

British Pat. No. 2059051 discloses a device for measuring the aggregation of particles at a wall, or among each other, the particles being dispersed in a fluid or gas flow. The fluid or gasous multi-phase system is directed onto a transparent wall and illuminated. The light which is scattered, reflected or attenuated by absorption is directed onto a detector, and evaluated. The measuring of the aggregation of the particles among each other, or at the wall works only with highly dilute dispersions that are transparent. It does not apply to highly concentrated dispersions as magnetic coating compositions in general, because these are opaque.

2. Summary Of The Invention

An object of the present invention is providing for the measuring of the properties characterizing a magnetic particle dispersion which is furthermore suitable of being the basis for a continuous measuring and control of the magnetic properties of the coating composition.

In the present invention, this object is achieved in that the coating composition is exposed to an alternating magnetic field of variable frequency, that the signal induced by the alternating magnetic field is received in the coating composition, and consequently that the susceptibility thereof is measured as a factor of the variable frequency, and evaluated with respect to the degree of dispersion, to the particle density, and to the viscosity of the coating composition.

The advantages presented by the invention substantially consist in that via the quality of the coating composition direct data can be supplied with respect to the characteristics degree of dispersion, particle density and viscosity.

This arrangement can thus be used for continuously controlling the characteristics and quality of the coating composition during its production and processing.

BRIEF DESCRIPTION OF THE DRAWINGS

In the following, the invention will be described in detail with reference to a drawing which merely represents one embodiment. The figures depict the following.

DESCRIPTION OF THE PREFERRED EMBODIMENT

Figure 1:
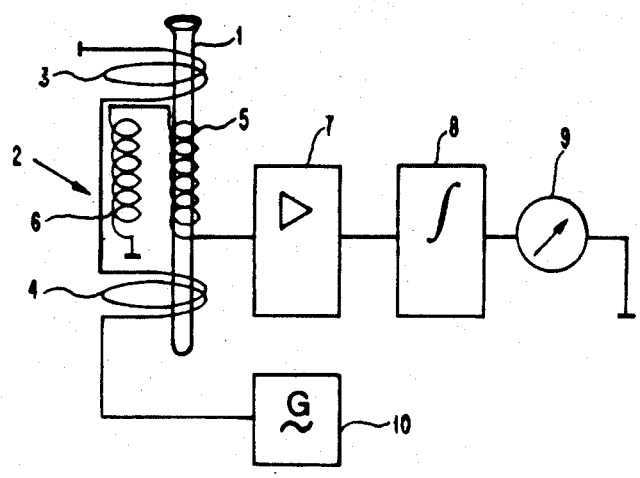
FIG. 1 is a schematic block diagram of a first embodiment of the the invention.

FIG. 1 depicts in a block diagram a first embodiment of the invention. The coating composition to be examined is provided in a vessel 1 which can resemble a test tube. This vessel 1 is placed with its coating composition in a coil arrangement 2. Coil arrangement 2 consists of two field coils 3 and 4 generating the energizing alternating magnetic field, and can e.g. form a so-called pair of Helmholtz coils. Coil arrangement 2 furthermore comprises a measuring coil 5 and a compensating coil 6. Compensating coil 6 is identical with measuring coil 5, but it does not surround vessel 1 containing the coating composition to be examined. The two coils 5 and 6 are preferably placed symmetrically in the field configuration generated by the two coils 3 and 4. It is thus made sure that the influence of the energizing field of coils 3 and 4 is simply eliminated from the measuring result by compensating coil 6.

Measuring coil 5 is connected to compensating coil 6, and to an amplifier 7 and an integrator 8. The measured result from integrator 8 is displayed on a voltmeter 9.

The two field coils 3 and 4 are fed by a function generator 10 which applies to the coils a sinusoidal-shaped current of variable frequency to generate an alternating magnetic field of variable frequency between the two coils 3 and 4 to which the sample coating composition in vessel 1 is exposed. The coating composition reacts in accordance with its composition, and induces a signal in measuring coil 5. In compensating coil 6, only the signal of the field between coils 3 and 4 is induced so that amplifier 7 receives only that measuring signal which supplies information on the voltage influenced by the coating composition. This voltage represents the susceptibility of the coating composition and is amplifed in amplifer 7, integrated in integrator 8, and finally displayed on voltmeter 9.

The frequency of the alternating magnetic field is changed by means of generator 10 between approximately 1 and 100 cps, and respectively passed through successively. The time during which the generator is continuously passed through from the frequency 1 cps to the frequency 100 cps is set in such a manner that each frequency is maintained at least until an induced signal which corresponds to that frequency arrives at measuring coil 5. In practical application, a period of approximately 10 seconds can be sufficient during which the range from 1 cps to 100 cps is passed through, and can subsequently be again passed through. Measuring takes place in the frequency range between 1 and 100 cps, with minimum fields as small as possible. The field intensity that is generated by the current supplied by function generator 10, and by means of coils 3 and 4, is to be so small that the field gradients at the ends of coils 3 and 4 do not effect any undesired magnetostatically caused coagulation of the particles of the coating composition, i.e. the coating composition is not to be altered. On the other hand, the field intensity has to be high enough for there appearing in measuring coil 5 a signal that is induced by the coating composition, and measurable. The field intensity selected is preferably less than 10 Oerstedt.

For highly dilute particle systems, i.e. for systems which contain so few particles that they are without any mutual interaction, it can be demonstrated that from measuring the susceptibility and the phase angle between the energizing field of coils 3 and 4 and the field induced in the measuring coil 5, conclusions can be made with respect to the particle density, the degree of dispersion, and the viscosity of the coating composition.

Figure 2:
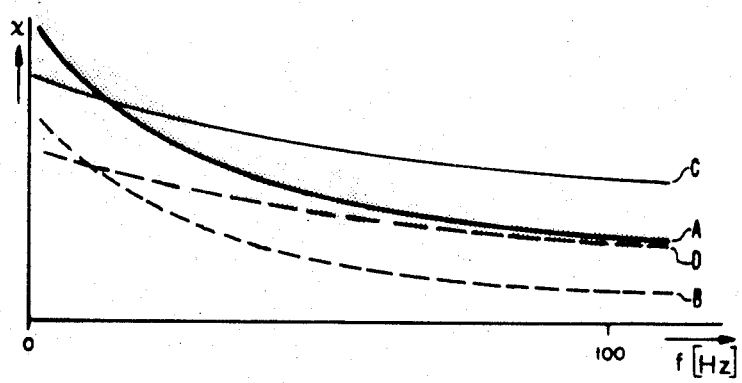
FIG. 2 is a graph showing the susceptibility as a function of the frequency for different property values.

However, for the very high particle density usual in magnetic disk technology, such interdependence can be determined only empirically. FIG. 2 depicts in curves A to D various courses of the susceptibility as a function of frequency f. To give an example, the continuous curve A represents the course of susceptibilty over frequency f for a coating composition having its magnetic properties within the desired limits, and thus represents a standard example. Over and beneath the curve, the tolerance range is given in dotted lines. The dashed curve B which in the overall range extends substantially in parallel to curve A and which presents lower values of susceptibility and consequently and magnetization of the suspension shows that the coating composition does not contain enough particles. Curve C which extends in the range of lower frequencies beneath standard curve A and in the range of higher frequencies, approximately from 15 to 20 cps, above standard curve A indicates that the suspension has an insufficient viscosity. Curve D which in the scope of lower frequencies extends far below standard curve A, and in the range of higher frequencies only slightly beneath standard curve A states that the associated coating composition has an insufficient degree of dispersion.

The measuring signal induced in measuring coil 5 is composed of two different parts. the first part refers to the change of magnetization of the individual particles. This change of magnetization is to be measured with rigidly fixed particle clusters. The phase between the energizing field and the measuring signal equals zero in the respective frequency range from 1 to 100 cps. The second part is based on the physical oscillation of the individual particles in the viscous liquid. The phase between the induced measuring signal and the energizing field is greater than zero in the respective frequency range between 1 and 100 cps. Owing to the phase-sensitive or rigidly coupled amplification in the lock-in amplifier 20 in FIG. 3, a discrimination between the two parts is made. By measuring the phase angle, or by using the lock-in amplifier, respectively, the evaluation of the signal induced with respect to degree of dispersion, viscosity, and particle density is of higher informative value.

In the arrangement of FIG. 1, the coating composition to be examined is provided in a vessel 1 closed at the bottom. The coating composition has a tendency of sedimentation, i.e. of the precipitation of heavier particles in downward direction, It is therefore advisable to measure the coating composition while it is moving. Vessel 1 can therefore be replaced by a pipe 11 through which the coating composition is guided.

Figure 3:
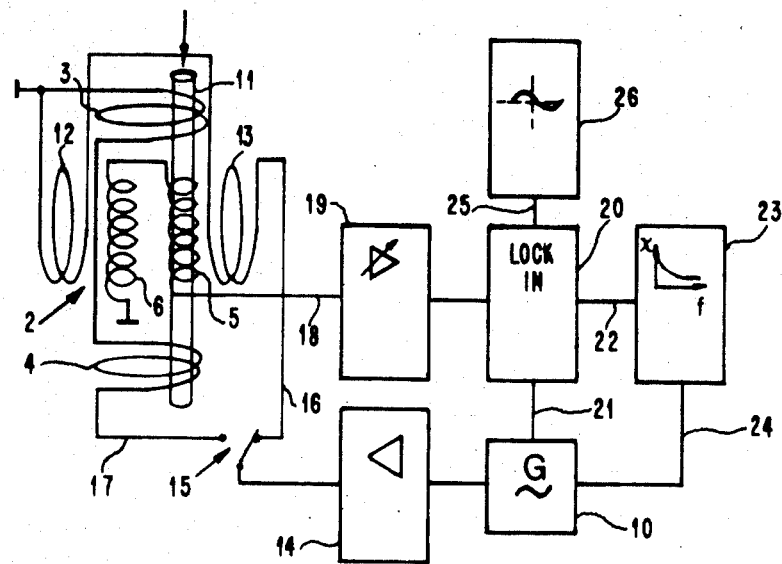
FIG. 3 is a schematic block diagram of a second embodiment of the invention, and FIG. 4 schematically shows the installation of the arrangement for practicing the invention in the bypass line of a storage vessel for the coating composition.

Such an arrangement with pipe 11 is depicted in FIG. 3 in connection with another coil arrangement 2. It is of course possible to replace in coil arrangement 2 vessel 1 of FIG. 1 by a pipe 11. Apart from coil pair 3 and 4 the arrangement of FIG. 3 includes a coil pair with coils 12 and 13. This coil pair can thus generate an alternating magnetic field of variable frequency vertically to the alternating magnetic field of variable frequency of coils 3 and 4. For that purpose, function generator 10 supplies current via a voltage-to-current converter 14 and a switch 15, either via line 16 to coils 12 and 13, or with an activated switch 15 via line 17 to coils 3 and 4. In this specific embodiment therefore the generation of the alternating fields in parallel to the longitudinal axis of pipe 11 by coils 3 and 4, or vertically thereto by coils 12 and 13 is effected not simultaneously but separately.

The voltage induced by the alternating magnetic fields in measuring coil 5 is applied via a line 18 to an amplifier 19 with a variable degree of amplification. This amplifier 19 can be an operational amplifier. The amplified signal is applied to lock-in amplifer 20 which receives via line 21 signals from function generaor 10. By means of this reference signal it is ensured that in lock-in amplifier 20 the amplification takes place in a phase-locked mode, i.e. that only those parts are amplified in the signal of measuring coil 5 which respectively correspond to the same frequency of function generator 10, and the same phase. Thus, only the desired signal and no noise signals are processed. This is advantageous particularly in the low frequency range. In lock-in amplifier 20, the signal supplied by amplifier 19 is furthermore rectified, and integrated from a time point of view, Via an output line 22, this rectified and integrated signal is applied to a recorder 23 which registers the voltage at output line 22 as a function of measuring frequency f. Measuring frequency f is applied by function generator 10 via a line 24 to device 3. The signal on line 22 which is represented and recorded by the recorder in a frequency-dependent mode can be interpreted as a measure for the time mean of the magnetization of the suspension.

Figure 4:
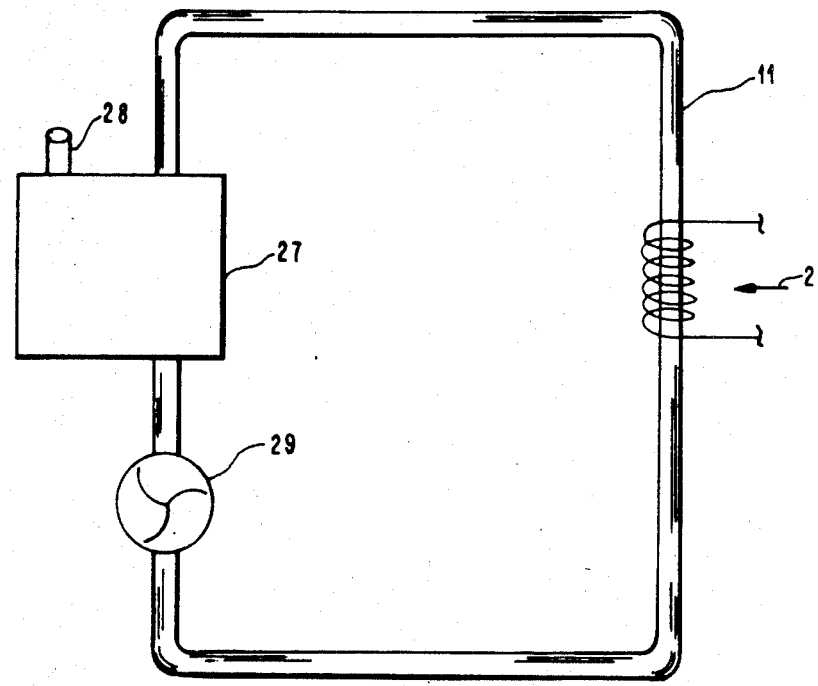

Lock-in amplifier 20 is connected via another line 25 to an oscilloscope 26. The oscilloscope thus permits the representation of the non-integrated signal of measuring coil 5 which represents the susceptibility of the magnetic coating composition flowing in pipe 11. Usually, the magnetic coating composition is contained in a tank 27, as depicted in FIG. 4. The composition is removed via a pipe 28, and in order to avoid sedimentation it is kept moving by a pump 29 and a bypass pipe 11. Coil arrangement 2 is provided around this pipe 11.

The magnetic susceptibility of the coating composition can be measured with the arrangement according to FIG. 3 in parallel to the flow direction of the composition through pipe 11. Coils 3 and 4 are used for this purpose, and switch 15 is in the position not shown, so that generator 10 feeds these coils via line 17.

While passing through pipe 11, the needle-shaped magnetic particles align in parallel to the flow direction. This degree of alignment is better if the degree of dispersion of the composition is high, and it is worse if the coating composition contains many lumps. If the particles are energized in parallel to the flow direction of the magnetic field of coil pair 3 and 4 a predetermined value is obtained. If the particles of the coating composition are energized vertically to the flow direction by the field of coils 12 and 13, for which purpose function generator 10 via switch 15 is activated as depicted in FIG. 3, and via line 16 feeds the coils, a value can again be obtained for the magnetizing of the coating composition. The difference of the measurings in parallel and vertical to the flow direction is an indicator of the degree of alignment of the coating composition. This degree of alignment is in turn a measure of the degree of dispersion because agglomerations or lumpings, respectively, do not align. Because the measuring process can be effected in such a manner that the magnetic coating composition particles can be energized either in parallel to the flow direction or vertically thereto, it is possible to make a precise statement on the magnetic characteristics of the coating composition. Furthermore, measuring can take place continuously so that it is particularly suitable for a continuous control of the properties of the coating composition. On the basis of these measurings statements can be made regarding the applicability of the coating composition, and if necessary, controlling steps can be initiated to improve the coating composition.

During measuring in the arrangement according to FIG. 3, or generally when measuring a coating composition flowing through a pipe 11 the flow speed should be maintained just so high that a specific magnetic particle which during the longest periodic interval just enters the field on the one side does not yet exit from the field on the other side. In other words. the flow speed must be lower than the coil dimension of the field coil divided by the longest periodic interval.

We claim:

1. A method of determining the degree of dispersion, particle density or viscosity of a magnetic coating composition comprising magnetic particles in a fluid resin/-solvent mixture, the method comprising the steps of:

generating an alternating magnetic field with an energizing coil assembly;

varying the frequency of the alternating magnetic field over a predetermined frequency range from an initial frequency value to a final frequency value;

surrounding the coating composition with a magnetic field sensing coil;

connecting the sensing coil to a magnetic field compensating coil located adjacent to the sensing coil, the step of connecting including orienting the compensating coil so that its winding is opposite the winding of the sensing coil and its axis is generally parallel to the axis of the sensing coil;

simultaneously exposing the coating composition, its surrounding sensing coil and the adjacent compensating coil to the varying-frequency alternating magnetic field of the energizing coil assembly;

measuring, over said predetermined frequency range and from the sensing coil and connected compensating coil, a signal representative of only the magnetic field induced in the coating composition by the varying-frequency alternating magnetic field of the energizing coil assembly, the step of measuring including correlating each measured signal value with a corresponding value of frequency of the alternating magnetic field; and comparing the values of the measured signal over said predetermined frequency range with empirically determined values over said frequency range, the empirically determined values representing a coating composition of desired dispersion, particle density or viscosity.

2. A method in accordance with claim 1, characterized in that said frequency varies between 1 and 100 cps.

3. A method in accordance with claim 1, characterized in that the properties of said composition are defined at a minimum field intensity of said alternating magnetic field, said field intensity being sufficiently low to prevent a change of said magnetic coating composition, and sufficiently high to generate a measurable signal.

4. A method according to claim 1 wherein the step of measuring the signal includes the step of measuring the phase angle between the varying-frequency alternating magnetic field and the signal representative of the magnetic field induced in the coating composition.

5. A method of determining the degree of dispersion, particle density or viscosity of a magnetic coating composition comprising magnetic particles in a fluid resin/solvent mixture, the method comprising the steps of:
generating an alternating magnetic field with an energizing coil assembly;
varying the frequency of the alternating magnetic field over a predetermined frequency range;
surrounding the coating composition with a magnetic field sensing coil;
connecting the sensing coil to a magnetic field compensating coil located adjacent to the sensing coil, the step of connecting including orienting the compensating coil so that its winding is opposite the winding of the sensing coil and its axis is generally parallel to the axis of the sensing coil;
simultaneously exposing the coating composition, its surrounding sensing coil and the adjacent compensating coil to the varying-frequency alternating magnetic field of the energizing coil assembly; and
measuring, over said predetermined frequency range and from the sensing coil and connected compensating coil, a signal representative of only the magnetic field induced in the coating composition by the varying frequency alternating magnetic field of the energizing coil assembly, the signal measuring step further comprising measuring a signal representative of the induced magnetic field in a first direction and then measuring a signal representative of the induced magnetic field in a second direction generally perpendicular to the first direction.

* * * * *